United States Patent [19]

Weier

[11] Patent Number: 5,479,938
[45] Date of Patent: Jan. 2, 1996

[54] LUMEN DIAMETER REFERENCE GUIDEWIRE

[75] Inventor: Steven D. Weier, Miramar, Fla.

[73] Assignee: Cordis Corporation, Miami Lakes, Fla.

[21] Appl. No.: 192,506

[22] Filed: Feb. 7, 1994

[51] Int. Cl.$^6$ ...................................................... A61B 5/00
[52] U.S. Cl. .............................................. 128/772; 128/657
[58] Field of Search ................................... 128/657, 666, 128/772; 609/93, 95, 164, 166, 170, 280, 282

[56] References Cited

U.S. PATENT DOCUMENTS

| | | |
|---|---|---|
| 3,706,883 | 12/1972 | McIntyre . |
| 4,279,252 | 7/1981 | Martin . |
| 4,559,046 | 12/1985 | Groshong et al. ................. 128/772 |
| 4,669,465 | 6/1987 | Moore et al. . |
| 4,724,846 | 2/1988 | Evans, III ......................... 128/772 |
| 4,793,359 | 12/1988 | Sharrow . |
| 4,932,419 | 6/1990 | De Toledo ..................... 128/657 X |
| 4,957,110 | 9/1990 | Vogel et al. . |
| 4,964,853 | 10/1990 | Sugiyama et al. . |
| 5,084,022 | 1/1992 | Claude . |
| 5,114,401 | 5/1992 | Stuart et al. . |
| 5,144,959 | 9/1992 | Gambale et al. . |
| 5,174,302 | 12/1992 | Palmer . |
| 5,209,730 | 5/1993 | Sullivan . |
| 5,222,949 | 6/1993 | Kaldany ............................ 604/282 |
| 5,253,653 | 10/1993 | Daigle et al. . |
| 5,259,393 | 11/1993 | Corso, Jr. et al. ................. 128/772 |
| 5,267,574 | 12/1993 | Viera et al. . |
| 5,353,808 | 10/1994 | Viera ................................. 128/722 |

FOREIGN PATENT DOCUMENTS

93/08862 5/1993 WIPO ................................. 128/772

*Primary Examiner*—Sam Rimell
*Attorney, Agent, or Firm*—Thomas R. Vigil

[57] ABSTRACT

The lumen diameter reference guidewire comprises: a central core wire; a coiled spring wire surrounding a distal portion of the core wire; a tip member; the coiled spring wire being fixed at its distal end to the tip member; and, the guidewire having in an distal area thereof proximal of the coiled spring wire, a plurality of markers which are highly radiopaque, each marker having the same precise length and the distance between adjacent markers varying from marker to marker.

10 Claims, 2 Drawing Sheets

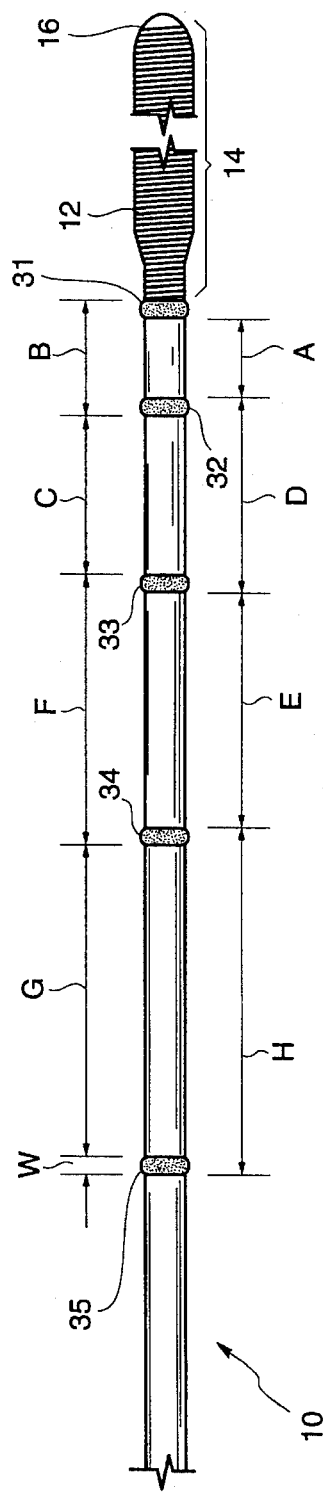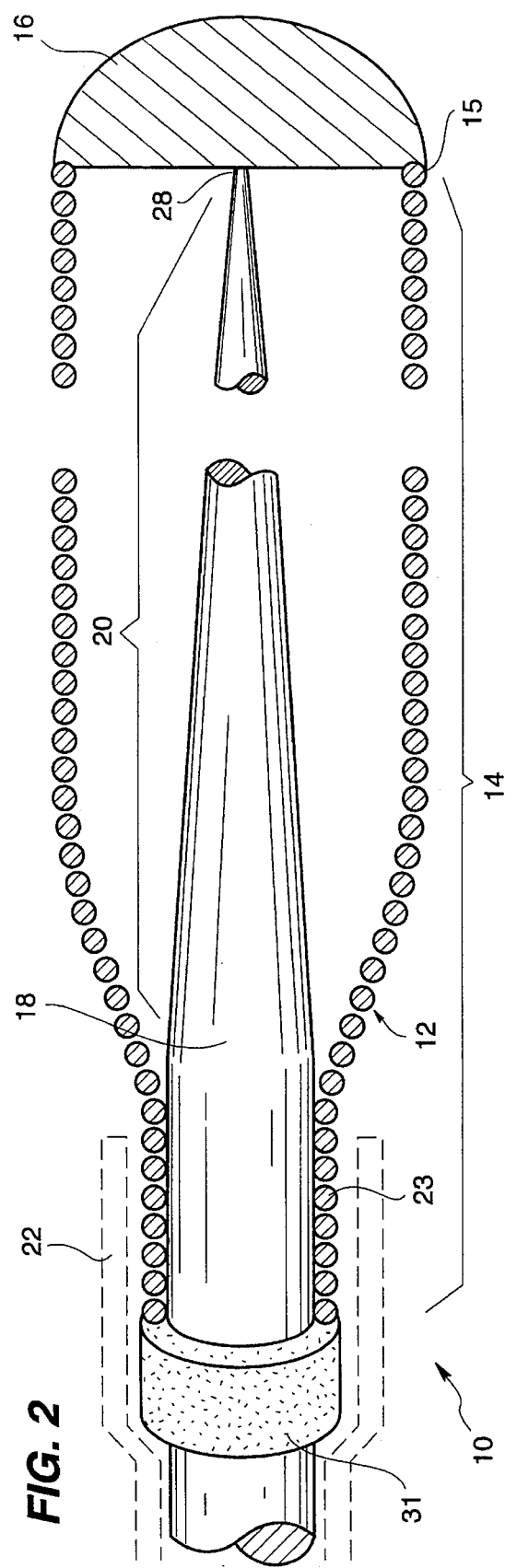
FIG. 1
FIG. 2

LUMEN DIAMETER REFERENCE GUIDEWIRE

BACKGROUND OF THE INVENTION

1. Field of the Invention

The present invention relates to a guidewire having marker bands strategically placed along a distal portion of the guidewire. More specifically, marker bands having the same precise width are placed at varying distances on and along the distal portion of the guidewire whereby the marker bands and the distance between adjacent marker bands can provide a scaling function to enable a physician to gauge fairly accurately the length of an area of stenosis in a blood vessel and to gauge fairly accurately the reduced diameter of the passageway through the area of stenosis.

2. Description of the related art including information disclosed under 37 CFR §§ 1.97–1.99

Heretofore, various guidewires with markers have been proposed. Examples of several previously proposed guidewires with markers are disclosed in the following U.S. Pat. Nos:

| U.S. Pat. No. | Patentee |
| --- | --- |
| 4,957,110 | Vogel et al. |
| 5,084,022 | Claude |
| 5,114,401 | Stuart et al. |
| 5,174,302 | Palmer |
| 5,253,653 | Daigle et al. |
| 5,267,574 | Viera et al. |

The Vogel et al. U.S. Pat. No. 4,957,110 discloses a steerable guidewire having electrodes for measuring vessel cross-section.

The Claude U.S. Pat. No. 5,084,022 discloses a graduated guidewire having spaced indicia to indicate the distance that the guidewire is extended into a vessel of a vascular system.

The Stuart et al. U.S. Pat. No. 5,114,401 discloses a guidewire having marks thereon that are used to establish, and maintain as constant, the position of a guidewire in a vascular system. The markings are uniformly spaced along a guidewire having a J-shaped distal end.

The Palmer U.S. Pat. No. 5,174,302 discloses a guidewire with spaced, highly radiopaque regions including radiopaque bands. The bands are located at spaced locations to provide a reference to a physician for positioning the guidewire and a balloon thereon.

The Daigle et al. U.S. Pat. No. 5,253,653 discloses a fluoroscopically viewable guidewire for catheters which includes a core wire having a reduced-in-diameter distal end portion that extends to a rounded distal tip member. A coiled spring wire extends from a larger-in-diameter portion of the coiled wire to and is fixed to the distal tip member in a distal region of the guidewire. Mounted on the reduced-in-diameter distal end portion of the core wire are spaced apart rings or discs which are highly radiopaque forming markers. The markers are arranged in a predetermined spaced relation. In one embodiment, the spacing between the markers is approximately 1 cm.

The Viera et al. U.S. Pat. No. 5,267,574 discloses a guidewire including a core wire having between three and nine marker bands thereon located just proximal of a coiled wire spring tip. The marker bands are placed between one and three centimeters apart along a tapering portion of the core wire.

SUMMARY OF THE INVENTION

According to the present invention there is provided a lumen diameter reference guidewire comprising: a central core wire; a coiled spring wire surrounding a distal portion of the core wire; a tip member; the coiled spring wire being fixed at its distal end to the tip member; and, the guidewire having in a non-tapered distal area thereof immediately proximal of the coil spring wire, a plurality of markers which are highly radiopaque, each marker having the same precise length which is a precise fraction of a millimeter and having predetermined millimeter distances between adjacent markers varying in precise increments from marker to marker so that the markers provide a scale to a position whereby the physician can accurately determine distances inside a blood vessel using the markers independently or in conjunction with each other.

BRIEF DESCRIPTION OF THE DRAWINGS

FIG. 1 is a longitudinal plan view of a guidewire constructed according to the teachings of the present invention having bands located at varying distances from each other in an area of the guidewire behind a coiled spring wire tip portion thereof.

FIG. 2 is an enlarged sectional view of the coiled spring wire at the tip of the guidewire and the most distal band mounted on the guidewire.

DESCRIPTION OF THE PREFERRED EMBODIMENT(S)

Figure 3:
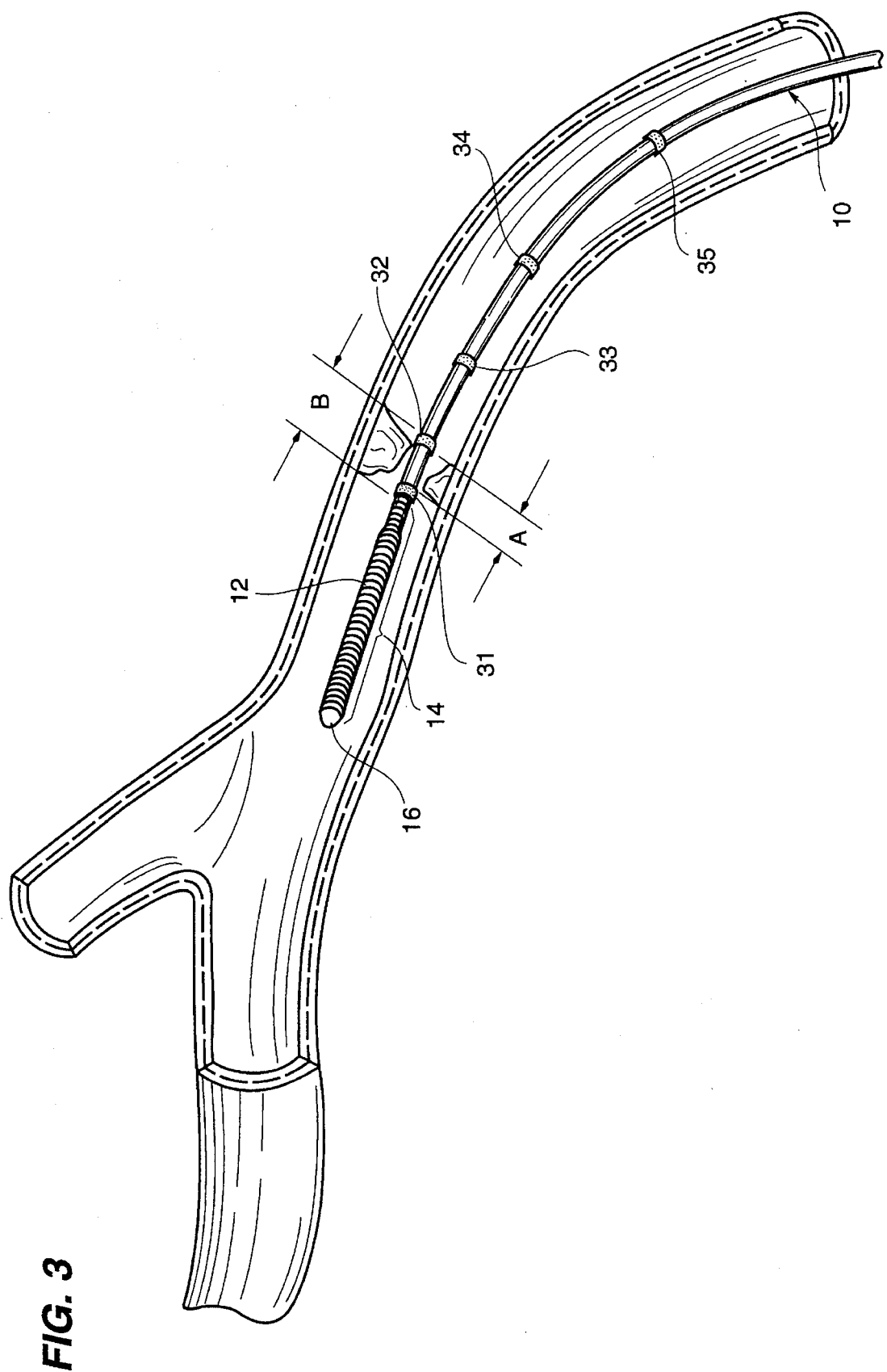
FIG. 3 is a longitudinal plan view of the guidewire received in a blood vessel and through an area of stenosis, the blood vessel being cut away to better show the guidewire.

Referring now to FIG. 1, there is illustrated therein a reference wire or guidewire 10 constructed according to the teachings of the present invention. The guidewire 10 comprises a coiled spring wire 12 which is situated in a distal end portion 14 of the guidewire 10 and which is fixed at its distal end 15 to a rounded tip member 16. The guidewire 10 further includes a central core wire 18 which reduces in diameter in a distal end portion 20 of the core wire 18. The distal end 15 of the coiled spring wire 12 and a distal end 28 of the reduced-in-diameter, tapered, distal end portion 20 of the central core wire 18 are fixed, such as by welding, brazing or soldering to the tip member 16.

If desired, a sleeve 22 made of a polymer material can be placed over the core wire 18, as shown in FIG. 2, in a manner similar to the sleeve disclosed in the Viera U.S. Pat. No. 5,267,574. The sleeve 22 can extend from a proximal area of the guide wire 10 to a necked down proximal end 23 of the coiled spring wire 12.

According to the teachings of the present invention, a plurality of markers or marker bands 31, 32, 33, 34 and 35, preferably defined by metal bands cut from a thin walled metal tubing of small diameter, are positioned along the length of the guidewire 10 in the area just proximal to the coiled spring wire 12. Each marker band 31–35 can be rounded or beveled at its edges to facilitate insertion of the guidewire 10 in a blood vessel. Note that, if desired and as shown in FIG. 2, the sleeve 22 can cover marker band 31 and proximal end 23 of the coiled spring wire 12 adjacent the marker band 31.

In the illustrated embodiment, five marker bands 31 . 35 are shown, each preferably having a width W of 0.25 mm. The markers 31–35 are progressively spaced further apart proximally of the distal end portion 14 of the coiled spring wire 12. The first marker 31 is spaced a distance A which is approximately 1 mm from the second marker 32 measured from the closest edges of the marker bands 31 and 32. Then, a distance B between the further most edges of the marker bands 31 and 32 is approximately 1.5 mm.

Then, in a similar manner the distance C between the closest edges of the second and third marker bands 32 and 33 is approximately 2 mm and the distance D between the furthest edges of the second and third bands 32 and 33 is approximately 2.5 mm. Then, the distance E between the closest edges of the third band and fourth bands 33 and 34 is 3 mm and the distance F between the furthest edges of the third and fourth bands 33 and 34 is approximately 3.5 mm. Finally, the distance G between the closest edges of the fourth and fifth marker bands 34 and 35 is approximately 4 mm and the distance H between the furthest edges of the fourth and fifth bands 34 and 35 is approximately 4.5 mm.

With this construction of the lumen diameter reference guidewire 10, the distances just described above can serve a scaling function for use by a physician. This is illustrated in FIG. 3 where the first section or distance A is positioned in an area of stenosis showing that the length is between 1 and 1.5 mm. This information can be used by a physician in determining the length of a balloon catheter to be used in an angioplasty procedure. Also, by eye-balling the distance across the open area in the area of stenosis relative to the distance between marker bands 31–35, the physician can make an approximation of the diameter of the open area and then make a determination of the size of balloon to use in performing an angioplasty procedure.

From the foregoing description it will be apparent that the lumen diameter reference guidewire 10 of the present invention has a number of advantages some of which are listed below.

1. It can be used in a pre-angioplasty procedure for determining the balloon diameter selection.

2. Secondly, it can be used in a post angioplasty procedure for a restenosis or gauging (%) of the occluded area that has been distended.

3. It can serve a scaling function for measuring the length of stenosis for determining the length of stent to be used.

4. The guidewire 10 can be used as reference when oblique views during fluoroscopy distort the actual size of the area of stenosis and the blood vessel in which it is located.

5. Use of the guidewire 10 removes guesswork from determining critical dimensions which are made under time and visual constraints.

6. The guidewire 10 can be adapted to any guidewire configuration.

7. The varying distance between marker bands 31–35 allows the guidewire to be used as a gauge or serve a scaling function. In this way the guidewire 10 can be used as a measuring device (gauge) at the lesion cite.

8. The marker bands 31–35 of the guidewire 10 can be applied externally or incorporated in the body of the guidewire 10, although short sections of a thin wall metal tubing are preferred.

Also, it will be understood that modifications can be made to the lumen diameter reference guidewire 10 described above without departing from the teachings of the present invention. Accordingly, the scope of the invention is only to be limited as necessitated by the accompanying claims.

What is claimed is:

1. A lumen diameter reference guidewire comprising:

a central core wire;

a coiled spring wire surrounding a distal portion of said core wire;

a tip member;

said coiled spring wire being fixed at its distal end to said tip member;

said guidewire having in a non-tapered distal area thereof immediately proximal of the coiled spring wire, a plurality of markers which are highly radiopaque, each marker having the same precise width which is a precise fraction of a millimeter and which is designated "x" and having predetermined millimeter distances between adjacent markers, the predetermined distances varying in precise increments from marker to marker with the distance between the closest edges of the first two adjacent markers in a direction proximally from a distal end of said guidewire being 4x and the distance between the furthest edges of the two adjacent markers being 6x, so that the markers provide a scale to a physician whereby the physician can accurately determine distances inside a blood vessel using the markers independently or in conjunction with each other.

2. The lumen diameter reference guidewire of claim 1 wherein said markers are marker bands which are mounted on the outside of said guidewire.

3. The lumen diameter reference guidewire of claim 2 wherein said marker bands are defined by short sleeves or sections of a thin walled metal tubing which is highly radiopaque.

4. The lumen diameter reference guidewire of claim 2 wherein five marker bands are provided and the distance between the closest edges of adjacent marker bands in a direction proximally from a distal end of said guidewire are, respectively, approximately 1 mm, 2 mm, 3 mm and 4 mm.

5. The lumen diameter reference guidewire of claim 4 wherein the width of each marker band is approximately 0.25 mm such that the distance between the furthest, oppositely facing edges of adjacent marker bands is approximately 1.5 mm, 2.5 mm, 3.5 mm, and 4.5 mm.

6. The lumen diameter reference guidewire of claim 1 wherein each marker has a width of approximately 0.25 mm.

7. The lumen diameter reference guidewire of claim 1 wherein five markers are provided.

8. The lumen diameter reference guidewire of claim 5 wherein said markers are progressively spaced further apart in a proximal direction from a distal end of said guidewire.

9. The lumen diameter reference guidewire of claim 1 wherein the central core wire is surrounded by a sleeve of plastic material extending from a proximal area of said guidewire to a location near said distal portion of said core wire.

10. The lumen diameter reference guidewire of claim 9 including a highly flexible distal end portion extending from a distal end of said sheath to said tip member defined by said coiled spring wire and a tapered distal end portion of said core wire.

\* \* \* \* \*